United States Patent
DeVoe et al.

(10) Patent No.: US 11,772,099 B2
(45) Date of Patent: Oct. 3, 2023

(54) INTEGRATED THERMOPLASTIC CHIP FOR RAPID PCR AND HRMA

(71) Applicant: University of Maryland, College Park, MD (US)

(72) Inventors: Donald DeVoe, College Park, MD (US); Eric Kendall, College Park, MD (US); Alex Sposito, College Park, MD (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 16/927,303

(22) Filed: Jul. 13, 2020

(65) Prior Publication Data

US 2020/0338562 A1   Oct. 29, 2020

Related U.S. Application Data

(62) Division of application No. 15/488,070, filed on Apr. 14, 2017, now Pat. No. 10,710,083.

(60) Provisional application No. 62/323,200, filed on Apr. 15, 2016.

(51) Int. Cl.
| | |
|---|---|
| *B01L 7/00* | (2006.01) |
| *C12Q 1/686* | (2018.01) |
| *B01L 3/00* | (2006.01) |

(52) U.S. Cl.
CPC ........... *B01L 7/52* (2013.01); *B01L 3/502707* (2013.01); *C12Q 1/686* (2013.01); *B01L 2300/0645* (2013.01); *B01L 2300/0816* (2013.01); *B01L 2300/0887* (2013.01); *B01L 2300/1827* (2013.01); *B01L 2400/0406* (2013.01); *B01L 2400/0688* (2013.01)

(58) Field of Classification Search
CPC ................ B01L 7/52; B01L 3/502707; B01L 2300/0645; B01L 2300/0816; B01L 2300/0887; B01L 2300/1827; B01L 2400/0406; B01L 2400/0688; C12Q 1/686; C12Q 2527/101; C12Q 2565/629
See application file for complete search history.

(56) References Cited

U.S. PATENT DOCUMENTS

| | | | |
|---|---|---|---|
| 8,058,054 B2 | 11/2011 | Owen et al. | |
| 9,061,278 B2 | 6/2015 | Hasson et al. | |
| 2002/0055149 A1 | 5/2002 | Kopf-Sill | |
| 2004/0043479 A1 | 3/2004 | Briscoe et al. | |
| 2008/0164155 A1 | 7/2008 | Pease et al. | |
| 2010/0086991 A1 | 4/2010 | Fish | |
| 2011/0312700 A1 | 12/2011 | Facer et al. | |
| 2013/0164191 A1* | 6/2013 | Coursey | B01L 7/00 324/649 |
| 2016/0318019 A1* | 11/2016 | Ledden | B01L 3/502715 |

OTHER PUBLICATIONS

Roy et al., Lab Chip, 15, 406-416, November (Year: 2014).*
Giordano et al., Analytical Biochemistry, 291: 124-132, (Year: 2001).*
Koh et al., Anal. Chem., 75, 4591-4598, (Year: 2003).
Chung et al., J. Micro/Nanolith, MEMS MOEMS 9(3), 031006, Jul.-Sep. (Year: 2010).
Hetzbleck et al., Lab Chip, 8; 12(11): 1972-8. Apr. 23 (Year: 2012).
R. Muddu, Y. a Hassan, and V. M. Ugaz, "Rapid PCR thermocycling using microscale thermal convection," J. Vis. Exp., No. 49, pp. 1-5, Jan. 2011.
B. C. Giordano, J. Ferrance, S. Swedberg, a F. Huhmer, and J. P. Landers, "Polymerase chain reaction in polymeric microchips: DNA amplification in less than 240 seconds," Anal. Biochem., vol. 291, No. 1, pp. 124-132, Apr. 2001.
J. H. Son, B. Cho, S. Hong, S. H. Lee, O. Hoxha, A. J. Haack, and L. P. Lee, "Ultrafast photonic PCR," Light Sci. Appl., vol. 4, No. 7, p. e280, 2015.
J. Y. Chou and B. C. Mansfield, "Mutations in the glucose-6-phosphatase-alpha (G6PC) gene that cause type Ia glycogen storage disease.," Hum Mutat., vol. 29, No. 7, pp. 921-930, Jul. 2008.
T. I. Wallow, A. M. Morales, B. A. Simmons, M. C. Hunter, K. L. Krafcik, L.A. Domeier, S. M., Sickafoose, K. D. Patel, and A. Gardea, "Low-distortion, high-strength bonding of thermoplastic microfluidic devices employing case-II diffusion mediated permeant activation.," Lab Chip, vol. 7, No. 12, pp. 1825-1831, 2007.
J. Wu, R. Kodzius, W. Cao, and W. Wen, "Extraction, amplification and detection of DNA in microfluidic chip-based assays," Microchim. Acta, vol. 181, No. 13-14, pp. 1611-1631, Dec. 2014.

* cited by examiner

*Primary Examiner* — Cynthia B Wilder
(74) *Attorney, Agent, or Firm* — Rothwell, Figg, Ernst & Manbeck, P.C.

(57) ABSTRACT

The present invention relates to a microfluidic system including a temperature controller and a thermoplastic microfluidic chip that enables rapid PCR in a PCR chamber of the microfluidic chip. Thermal control of the PCR chamber is achieved by applying voltage to heater electrodes patterned directly onto one layer of the microfluidic chip. The temperature controller adjusts the voltage applied to the heater electrodes by changing temperature controller parameters selected to minimize duration of each PCR cycle. Furthermore, simple operation of the microfluidic chip is provided through using an integrated passive capillary valve, requiring minimum operator intervention and eliminating the need for fluidic interfacing, pumping, or metering during chip loading.

16 Claims, 7 Drawing Sheets

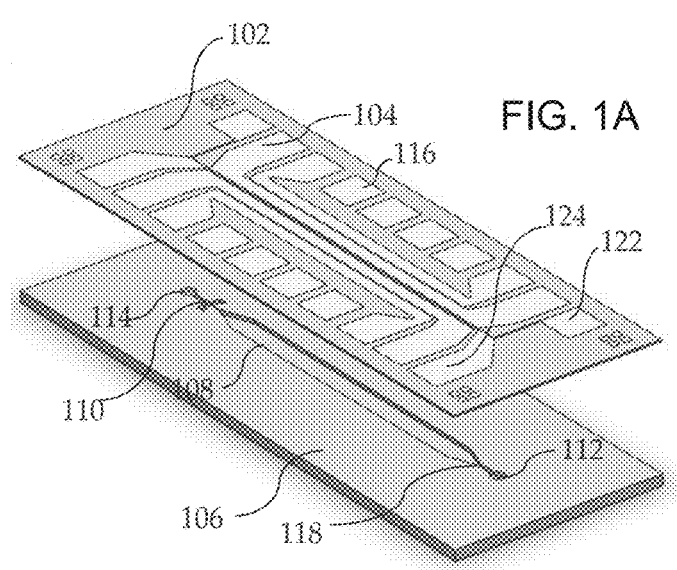
FIG. 1A
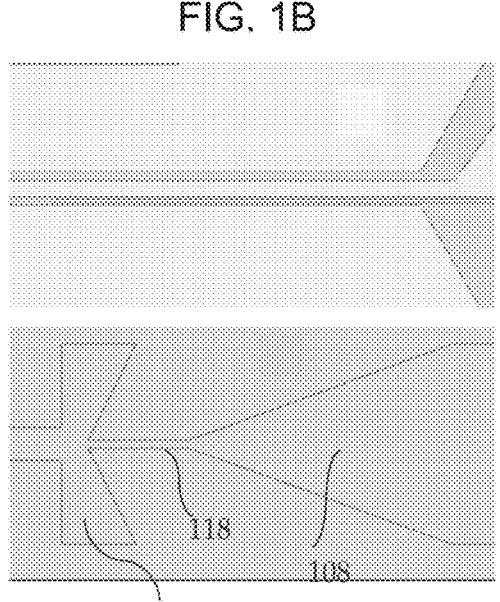
FIG. 1B
FIG. 1C
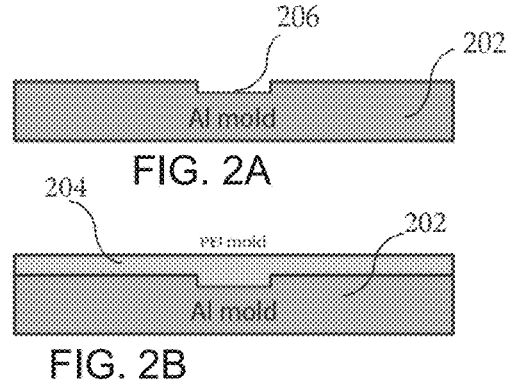
FIG. 2A
FIG. 2B
FIG. 2C
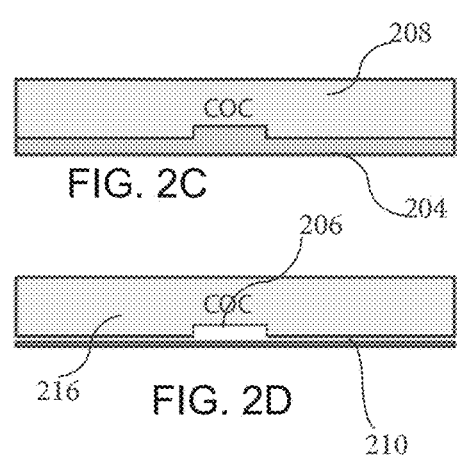
FIG. 2D
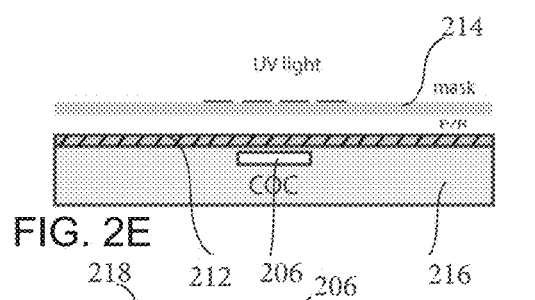
FIG. 2E
FIG. 2F
FIG. 2G
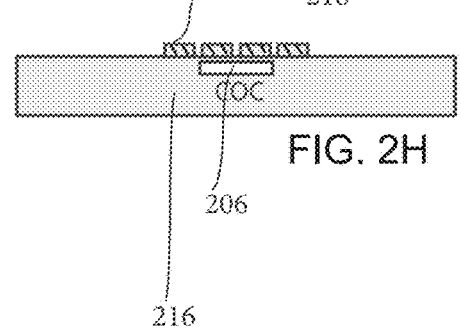
FIG. 2H

INTEGRATED THERMOPLASTIC CHIP FOR RAPID PCR AND HRMA

This application is a divisional of U.S. patent application Ser. No. 15/488,070, filed on Apr. 14, 2017, which claims the benefit of U.S. Provisional Patent Application Ser. No. 62/323,200, filed on Apr. 15, 2016, which is incorporated herein by reference in its entirety.

BACKGROUND

Field of the Invention

The present invention relates to a thermoplastic microfluidic device that enables rapid nucleic acid amplification, such as polymerase chain reaction (PCR), together with high resolution melt analysis (HRMA) of the resulting amplified product in a single integrated platform.

Discussion of the Background

Benchtop amplification and PCR platforms commonly employ large resistive or thermoelectric heating elements for temperature control, resulting in high power requirements and slow amplification times due to the large thermal masses involved. Together with high costs associated with benchtop PCR platforms, these limitations have constrained the wider use of PCR in point-of-care settings. For use as a near-patient diagnostic tool the ideal PCR system should support rapid sample-answer times using individual clinical samples, while offering simple operation in a small footprint. The system should also employ inexpensive and disposable PCR elements to minimize cost and infrastructure requirements, issues of particular concern for applications in global health care and resource-limited environments.

Microfluidic technology offers significant potential for overcoming these constraints and advancing PCR technology for point-of-care applications. The earliest PCR microsystems consisted of bulk-etched silicon reaction chambers with integrated thin film polysilicon heaters, where inherently low thermal mass and high surface area enabled rapid cycle times around 2 min. It is known in the art to employ a range of microfluidic PCR platforms that use integrated thin film heaters patterned on silicon or glass substrates containing sealed microchannels within which amplification occurs. While these microscale platforms have been shown to enable rapid PCR cycle times, the fabrication costs associated with bulk micromachining and sealing of both silicon and glass substrates can be prohibitive for many applications.

In contrast to these materials, thermoplastics offer significant advantages for the development of low-cost consumable microsystems. In particular, thermoplastics may be patterned using exceptionally low-cost replication techniques and a variety of rapid large-area bonding methods that are available for sealing the resulting microchannels. While a number of thermoplastic PCR chips have been reported, the high heat capacity and low thermal conductivity associated with engineering thermoplastics have resulted in thermal response times that prohibit rapid PCR. Several techniques based on non-contact heating have been explored to address the thermal limitations of thermoplastics, enabling their effective use as microfluidic substrates for rapid nucleic acid amplification. For example, Muddu et al. discloses 10 min PCR in a thermoplastic substrate using microscale convection to control the local surface temperature (R. Muddu, Y. a Hassan, and V. M. Ugaz, "Rapid PCR thermocycling using microscale thermal convection," *J. Vis. Exp.*, no. 49, pp. 1-5, January 2011). Giordano et al. demonstrated a cycle time of less than 4 min by using non-contact infrared heating of a polyimide microdevice (B. C. Giordano, J. Ferrance, S. Swedberg, a F. Hühmer, and J. P. Landers, "Polymerase chain reaction in polymeric microchips: DNA amplification in less than 240 seconds," *Anal. Biochem.*, vol. 291, no. 1, pp. 124-32, April 2001). Similarly, Son et al. employed non-contact plasmonic photothermal heating of a gold thin film to thermocycle poly-methyl methacrylate microwells, with amplification achieved in 5 min. (J. H. Son, B. Cho, S. Hong, S. H. Lee, O. Hoxha, A. J. Haack, and L. P. Lee, "Ultrafast photonic PCR," *Light Sci. Appl.*, vol. 4, no. 7, p. e280, 2015).

Accordingly, there is a need for a disposable thermoplastic microfluidic chip that enables rapid PCR together with high resolution melt analysis (HRMA) of the resulting PCR product in a single integrated platform.

SUMMARY OF THE INVENTION

The present invention relates to systems and methods for performing rapid amplification of nucleic acid in a reaction chamber, including PCR amplification, of a microfluidic chip. Specifically, in one aspect of the invention a microfluidic system comprising a microfluidic chip and a temperature controller is provided. The microfluidic chip comprises first and second thermoplastic layers. The first layer includes at least one inlet well in fluid communication with a PCR chamber and one or more hydrophilic capillary valves. The second thermoplastic layer has a first surface and a second surface. The first surface of the second thermoplastic layer has one or more heater and sensor electrodes patterned thereon. The heater electrodes control a temperature in the PCR chamber. The second surface of the second thermoplastic layer is bonded to the first thermoplastic layer sealing the PCR chamber. The temperature controller controls an input voltage applied to the one or more heater electrodes based on data provided by the one or more sensor electrodes indicative of the temperature in the PCR chamber. The input voltage is adjusted during each PCR cycle based on controller parameters selected to minimize duration of each PCR cycle.

In yet another aspect of the invention, a method for performing a rapid PCR reaction is provided.

Specifically, the method comprises providing a microfluidic chip comprising one or more heater and sensor electrodes, at least one inlet well in fluid communication with a PCR chamber, and one or more hydrophilic capillary valves, the heater electrodes controlling a temperature in the PCR chamber. The next step of the method relates to running a PCR reaction and controlling an input voltage applied to the one or more heater electrodes based on data provided by the one or more sensor electrodes indicative of the temperature in the PCR chamber. The input voltage is adjusted during each PCR cycle based on controller parameters selected to minimize duration of each PCR cycle.

In one embodiment, the controller parameters are selected based on data produced by a simulation model prior to a PCR reaction evaluating thermal performance of the microfluidic chip during a PCR cycle and/or each stage of a PCR cycle. In yet another embodiment the controller is a PID controller. In a further embodiment, the first and second thermoplastic layers are fabricated from cyclic olefin polymer or cyclic olefin copolymer. By way of example, the second thermoplastic layer is 50 µm thick and the reaction chamber is 200 μm deep. In a further aspect of the invention, the thickness of the second thermoplastic layer and the depth of the reaction chamber are selected to minimize the duration of a PCR cycle. Those of skill in the art will understand alternative thermoplastic materials having similar properties to those described herein, which can also be used in the practice of the invention.

In another aspect of the invention, a sample received at the input well flows towards the PCR chamber by a capillary action, the sample fluid being halted at the PCR chamber by the one or more hydrophilic capillary valves. By way of example, an expansion angle of the valve is provided at 150°. One or more valve(s) has a width of approximately 50 μm and a depth of approximately 20 μm. In yet another embodiment, the reaction chamber is matched to the one or more heater electrodes. Temperature sensing in the reaction chamber is performed by applying a small current to a first sensor electrode while monitoring a voltage drop across a second sensor electrode. Furthermore, the PCR reaction in the reaction chamber is followed by a high resolution melt analysis (HRMA) performed in the PCR chamber.

In yet another aspect of the invention, a method of manufacturing a chip is provided. Specifically, the method comprises milling channels in an aluminum mold; embossing polyetherimide (PEI) mold with aluminum mold; molding a resin layer onto the PEI mold to produce a wafer; exposing the wafer to a solvent and bonding the wafer to a thin film layer to form a microchannel; spinning a photoresist onto the wafer and photo-lithographically patterning the photoresist; developing the wafer; and depositing a thin metal layer on top of the wafer to form heater and sensor electrodes.

In one embodiment, the chip is a microfluidic chip that may be used for performing a PCR reaction and HRMA analysis. By way of example and without limitation, the resin layer and the thin film layer are fabricated from cyclic olefin polymer (COP) or cyclic olefin copolymer (COC). In yet another embodiment, the thin film layer is approximately 50 μm thick and the microchannel is 200 μm deep.

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements.

FIG. 1A demonstrates a 3D schematic of a microfluidic chip according to the present invention.

FIG. 1B demonstrates a close up view of the heater and sensor intersection as shown in FIG. 1A.

FIG. 1C demonstrates a schematic of the hydrophilic capillary valve of FIG. 1A.

FIG. 2A demonstrates the step of milling channels in aluminum (Al) mold.

FIG. 2B demonstrates the step of embossing polyetherimide (PEI) mold with alluminium mold.

FIG. 2C demonstrates the step of molding COP resin onto PEI mold.

FIG. 2D demonstrates the step of exposing COP wafer to decalin solvent and bonding the COP wafer to the COP thin film.

FIG. 2E demonstrates the step of spinning negative liftoff resist onto COP wafer and photolithographically patterning the resist.

FIG. 2F demonstrates the step of developing the COP wafer.

FIG. 2G demonstrates the step of depositing chromium (Cr) and gold (Au) on top of the COP wafer.

FIG. 2H demonstrates final COP wafer with Cr/Au elements.

DETAILED DESCRIPTION OF THE INVENTION

Figure 3A:
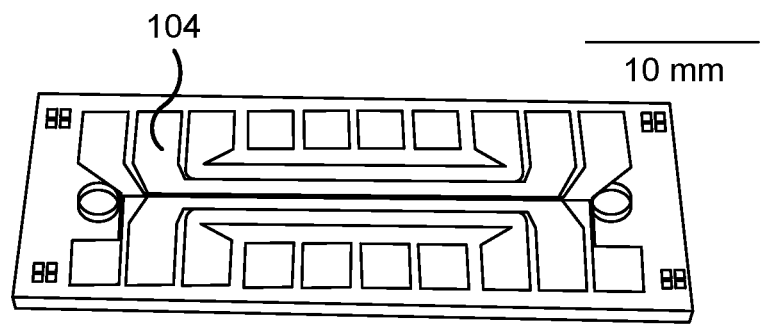
FIG. 3A is an image of the microfluidic chip according to the present invention taken from the bottom of the microfluidic chip.

The present invention has several embodiments and relies on patents, patent applications, and other non-patent references for details known in the art. Therefore, when a patent, patent application, or other non-patent reference is cited or repeated herein, it should be understood that it is incorporated by reference in its entirety for all purposes as well as for the proposition that is recited.

The present invention relates to a disposable thermoplastic microfluidic device (microfluidic chip) that enables rapid PCR together with high resolution melt analysis (HRMA) of the resulting PCR performed in the same reaction chamber. In addition to performing rapid PCR and HRMA in a low-cost format, the thermoplastic chips are designed to address several system-level issues which constrain established microfluidic PCR platforms. In one embodiment, the microfluidic chip is fabricated using a two-step embossing process compatible with high throughput replication-based manufacturing processes. By way of example and without limitation, cyclic olefin polymer (COP) or cyclic olefin copolymer (COC) may be used as a thermoplastic with low autofluorescence. Sealing of the COP microchannels is performed using a COP or COC film layer, thereby minimizing thermal resistance and mass of the PCR chips. Thermal control is achieved by patterning thin film metal electrodes directly onto the sealing COP film layer for combined temperature sensing and thermal actuation in a low-power format. In yet another embodiment, simple operation of the microfluidic chip according to the present invention is provided through self-loading of reaction volumes using an integrated passive capillary valve, requiring minimum operator intervention and eliminating the need for fluidic interfacing, pumping, or metering during chip loading. In a further embodiment, a fully self-contained system using a microcontroller is employed to implement all assay steps including thermocycling using closed-loop control scheme and fluorescence detection for assay readout. The disposable PCR chip according to the present invention successfully combines simple operation, rapid PCR, precise temperature control for accurate HRMA, and low cost in a compact format.

FIG. 1A demonstrates a 3D schematic of a microfluidic chip according to the present invention. The microfluidic chip comprises a first layer 106 and a second layer 102. Thin film heater electrodes 104, thin film metal sensor electrodes 122 and 124, and gold-coated spring contact pins 116 are patterned directly on one of surfaces of the second layer 102. The number of heater and sensor electrodes is not limited to the number as shown in FIG. 1A as the chip according to the present invention may comprise any number of heater and sensor electrodes. The first layer 106 is a microfluidic layer that comprises a reaction chamber 108, a passive capillary valve 110, a microchannel 118, an input well 112, and an air vent 114. The number of microfluidic features such as channels, chambers, valves, and wells is not limited the number shown in FIG. 1A as the chip according to the present invention may comprise any number of microfluidic features. The second layer 102 is bonded to the first layer sealing the microchannel 118 and the reaction chamber 108. In one embodiment, the first layer 106 and the second layer 102 are thermoplastic layers. By way of example and without limitation, the thermoplastic may be cyclic olefin polymer (COP). In yet another embodiment, sealing of the COP microchannel 118 and chamber 108 is performed using a 50 µm thick COP film layer. By way of example and without limitation, the imprinted reaction chamber may be 200 µm deep, while hydrophilic expansion valve regions are 20 µm deep.

Thermal control of a reaction in the reaction chamber 108 is achieved by the matching thin film heater electrodes 104 and thin film sensor electrodes 122, 124 patterned between the heater electrodes directly onto the second layer 102 for combined temperature sensing and thermal actuation. FIG. 1B demonstrates a close up view of the intersection of the heater and sensor electrodes patterned on the second thermoplastic layer 102. Temperature sensing in the reaction chamber 108 may be performed by applying a small current to the sensor electrode 124 while monitoring the voltage drop across the sensor electrode 122. In one embodiment, the reaction chamber 108 is used for performing a polymerase chain reaction (PCR). By way of example and without limitation, gold may be used for both the heater and sensor electrodes due to its linear temperature coefficient of resistance in the PCR temperature range. Other conductive materials having similar linear temperature coefficients of resistance as known to those of skill in the art can alternatively be used in the invention as provided herein.

FIG. 1C demonstrates a schematic of the passive capillary valve 110 in fluid communication with the microchannel 118 and the reaction chamber 108. Sample loading is performed by pipetting a sample into the inlet well 112 of the chip. As the sample is deposited into the inlet well 112, capillary action pulls the reaction mixture into the microchannel 118, resulting in automated filling of the reaction chamber 108. As the sample fills the reaction chamber 108, the liquid reaches a passive hydrophilic expansion valve 110 incorporated into the first chip layer 106 at the terminal end of the reaction chamber 108. The capillary expansion valve 110 consists of a sudden increase in the channel width, resulting in a Laplace pressure as curvature of the liquid/air interface is forced to increase while exiting the valve 110. At a sufficiently high Laplace pressure, the system reaches equilibrium and the fluid flow is halted.

Burst pressure for a capillary expansion valve is determined in part by the channel dimensions and the expansion angle, defined as the angle between the adjacent surfaces at the valve entrance, with larger expansion angles generally resulting in higher burst pressures. In one embodiment, to enhance burst pressure in the microfluidic chip according to the present invention, the width and depth of the valve region are reduced to 50 µm and 20 µm, respectively, while the expansion angle is set at 150°.

Figure 4:
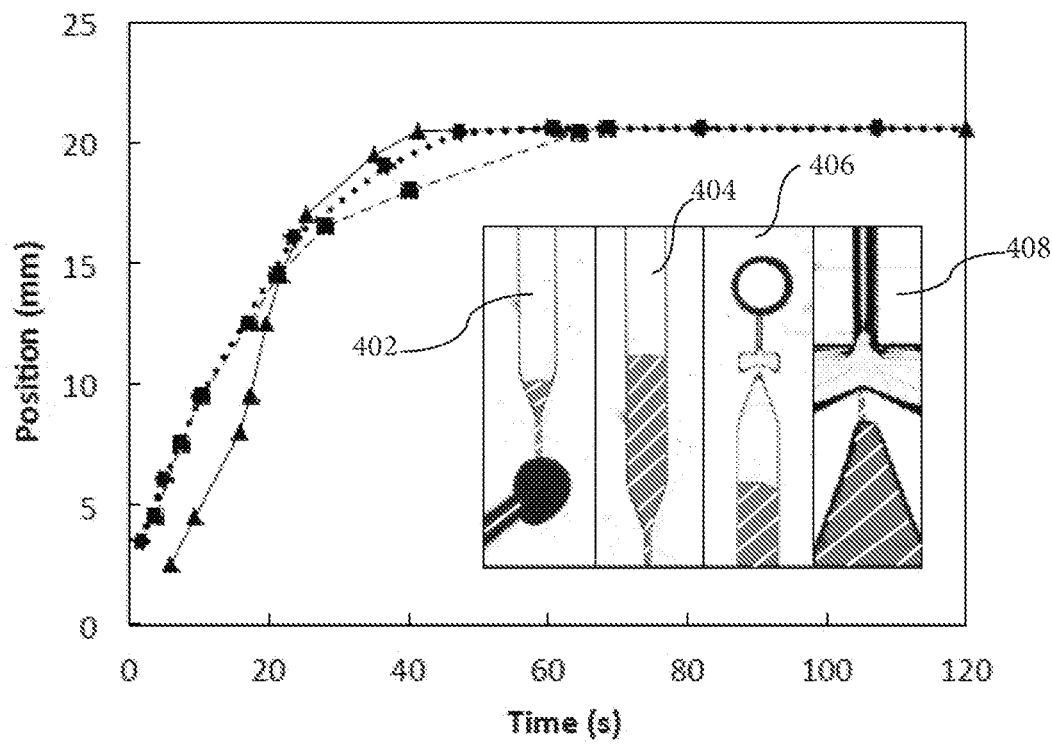
FIG. 4 is a plot of meniscus position (mm) versus time (s) for three different capillary loading and flow stop experiments.

During loading, capillary pumping of a sample results in consistent filling of the reaction chamber 108, with fluid reaching the expansion valve 110. Once reaching the valve 110, the capillary filling process halts and no further motion of the fluid is observed. FIG. 4 demonstrates the position of the leading edge of a fluid sample within the reaction chamber 108 as a function of the time for three independent filling experiments. These three experiments are represented by dots, triangles, and squares, respectively. Based on the graphical representation, it takes approximately 50 s for the sample fluid to fill the reaction chamber 108. In addition to the graphical representation, images 402-408 demonstrate different stages of the sample filling process. Specifically, in image 402, a sample fluid received at the input well 112 flows into the microchannel 118 and reaction chamber 108. The sample fluid is gradually fills the reaction chamber 108 in image 404 and approaches the valve 110 in image 106. In image 408, the equilibrium is achieved when the sample fluid stops at the capillary valve 110. This simple and robust passive loading method serves to reduce operational error while eliminating the need for complex fluidic interfacing or pumps during sample loading process.

FIGS. 2A-2H demonstrate a process for fabricating the microfluidic chip according to the present invention as shown in FIG. 1A. The microfluidic chip may be fabricated from COP or COC due to their high transparency, low autofluorescence, low water absorption, and low gas permeability. By way of example and without limitation, FIGS. 2C-2H demonstrate the process of fabricating the chip from COC. However, any suitable polymer, including COP and COC can be used. The process starts with milling a channel 206 in an aluminum mold 202 as demonstrated in FIG. 2A. Because channel features are milled directly into the initial aluminum mold 202, the aluminum surface can be easily polished after mold machining to ensure excellent optical quality in the final COP microfluidic chip. The next step, as shown in FIG. 2B, is directed to embossing a secondary mold 204 with the aluminum mold 202. Inverse features from the aluminum mold 202 are transferred to the secondary mold 204. In one embodiment, the secondary mold 204 is embossed from polyetherimide (PEI) that is a high strength and high transition temperature (Tg) thermoplastic. In one embodiment, to ensure compatibility with the high temperatures encountered in PCR, a grade of COP with a glass transition temperature (Tg) of approximately 135° C. is selected. The PEI secondary mold 204 proved to be very durable over many embossing cycles, and can be easily reproduced from the aluminum master as PEI mold tolerance degrades.

The next step demonstrated in FIG. 2C is directed to molding COP resin 208 onto the secondary PEI mold 204. Specifically, resin pellets are placed on the PEI secondary mold 204 and heated.

FIG. 2D demonstrates exposing a COP wafer 216 to a solvent and bonding a thin film 210 to the COP wafer 216. In one embodiment, the solvent is decalin. The multilayer substrate is then pressed at in a hot press to complete the bonding. The solvent bonding process allows for permanent sealing of the microchannel 206 without any observable deformation of the COP sealing film 210.

Thin film gold electrodes for temperature control are fabricated using a liftoff photoresist process. FIG. 2E demonstrates a negative liftoff photoresist 212 spun onto the COP wafer 216 and photolithographically patterned by using an optical mask 214. Alignment marks pre-molded into the COP microchannel layer 208 were used to position the optical mask 214 to precisely align the electrodes 104 under the reaction chamber 108 as shown in FIG. 1A. In the next step as shown in FIG. 2F, the photoresist 212 is developed. After developing the photoresist 212, a chromium adhesion layer and a gold layer 222 are sequentially deposited on top of the COP wafer 216 as demonstrated in FIG. 2G. In the final step, as shown in FIG. 2H, the photoresist 212 is removed by immersing the wafer 216 in an acetone bath.

Figure 3B:
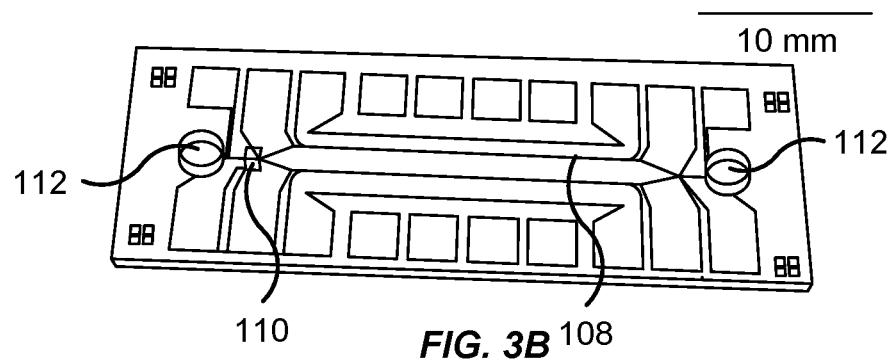
FIG. 3B is an image of the microfluidic chip according to the present invention taken from the top of the microfluidic chip.

Images of the microfluidic chip fabricated according to the process of FIGS. 2A-2H are illustrated in FIGS. 3A-3B. FIG. 3A is an image of the microfluidic chip according to the present invention taken from the bottom of the chip to demonstrate the gold heater and sensor electrodes 104, 122, and 124. FIG. 3B is an image of the chip according to the present invention taken from the top of the chip to show microfluidic features including the reaction chamber 108, input well 112, vent well 114, passive capillary valve 110, and microchannel 118.

Example 1. Microfluidic Chip Fabrication

A master mold was prepared by milling microscale features into a 15 cm square plate of 6061 aluminum using a computer numerical controlled 3-axis CNC machine (by way of example and without limitation, MDX-650, Roland DGA, Irvine, Calif.). After machining, the aluminum piece was polished to a mirror finish by chemical-mechanical polishing (by way of example and without limitation, MET-PREP 4, Allied High Tech Products Inc., Rancho Dominguez, Calif.). Inverse features from the aluminum mold were transferred to a secondary mold consisting of polyetherimide (by way of example and without limitation, Ultem PEI 1000) by embossing at 230° C. and 225 psi for 30 min using a hot press (by way of example and without limitation, AutoFour/15, Carver, Inc., Wabash, Ind.).

The microfluidic substrate was constructed of COP (by way of example and without limitation, Zeonex 1420R, Zeon Chemicals, Louisville, Ky.). Approximately 15 mL of resin pellets were placed on the PEI secondary mold and heated to 190° C. for 30 min in the hot press. Once heated, the pressure applied to the stack was increased in 50 psi increments every 10 min, and held at a final pressure of 250 psi for an additional 10 min. The resulting COP plaque had a thickness of approximately 550 μm. The imprinted reaction chamber was 200 μm deep, while hydrophilic expansion valve regions were 20 μm deep. Input ports were manually drilled using a drill press. The microfluidic substrate was sealed by a 50 μm thick COP film (by way of example and without limitation, Zeonex 1420R) using a solvent bonding technique modified from a previously developed procedure (T. I. Wallow, A. M. Morales, B. A. Simmons, M. C. Hunter, K. L. Krafcik, L. A. Domeier, S. M., Sickafoose, K. D. Patel, and A. Gardea, "Low-distortion, high-strength bonding of thermoplastic microfluidic devices employing case-II diffusion-mediated permeant activation.," Lab Chip, vol. 7, no. 12, pp. 1825-1831, 2007). The channel side was exposed to 35% decahydronaphthalene in ethanol (w/w) for 7 min, rinsed with 100% ethanol, and blown dry with N2. The multilayer substrate was then pressed at 200 psi and 50° C. for 15 min in a hot press to complete the bonding. Thin film gold electrodes for temperature control were fabricated using a liftoff resist process. Negative liftoff photoresist (by way of example and without limitation, NR9-3000PY, Futurrex Inc., Franklin, N.J.) was spun to a thickness of 3.7 μm on the exposed surface of the 50 μm COP layer and patterned by contact photolithography. Alignment marks pre-molded into the COP microchannel layer were used to position the mask to precisely align the electrodes under the reaction chamber. After developing the photoresist (by way of example and without limitation, RD6 developer, Futurrex Inc., Franklin, N.J.), a 15 nm chromium adhesion layer and 75 nm gold layer were sequentially deposited by e-beam evaporation (by way of example and without limitation, Denton Vacuum Explorer, Moorestown, N.J.), and photoresist was removed by immersing the wafer in an acetone bath under light agitation. The metallized COP wafer was cleaned with methanol, isopropanol, and deionized water, and individual chips (six to a wafer) were separated by CNC milling.

The term "ultrafast PCR" commonly refers to a PCR assay providing amplification times below 10 min. For a typical assay requiring 30 cycles for complete amplification, this implies a required cycle time on the order of 20 s. To determine geometric and thermal control parameters required for the thermoplastic PCR chip according to FIGS. 3A-3B to reach this target, numerical simulation models are used to evaluate the impact of chip dimensions on thermal response of the system. A temperature controller is used to dynamically control input voltage for heating elements (for example, heating electrodes 104 in FIG. 1A) in response to thermal sensors readings (for example, sensors 122, 124 in FIG. 1A). Temperature controller parameters are selected to minimize the duration of a PCR cycle. In one embodiment, the temperature controller parameters are selected based on a simulation model evaluating thermal performance of a microfluidic chip (for example, the chip of FIGS. 3A-3B) during a PCR cycle and/or each step (denature, annealing, extension) of the PCR cycle. Accordingly, the temperature controller parameters are selected prior to performing a PCR reaction and are fixed during the PCR reaction. The input voltage for heating elements is dynamically adjusted during the PCR reaction based on the preselected temperature controller parameters. The duration of each PCR step (denature, annealing, extension) is set in temperature controller software, with temperature held at a given set point for a fixed time. The temperature controller parameters dictate how quickly the temperature changes between PCR steps, and helps to maintain the set temperature once reaching the set point.

Realistic values are used for forced convective cooling of the chip surface and current density limits for the heater electrodes. Rise time, defined as the time required for the response to rise from 10% to 90% of the steady state value, is extracted from simulation models for various chip designs over a range of thicknesses for the COP sealing film 102

(FIG. 1A) as well as a range of reaction chamber depths in the microfluidic substrate 106 (FIG. 1A).

Figure 5A:
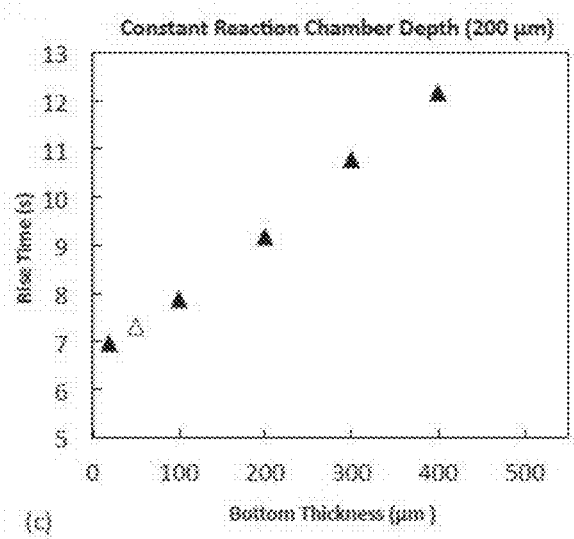
FIGS. 5A-5B relate to a parametric evaluation of different chip designs by plotting total rise time for a complete PCR cycle as a function of chip geometric dimensions.
Figure 5B:
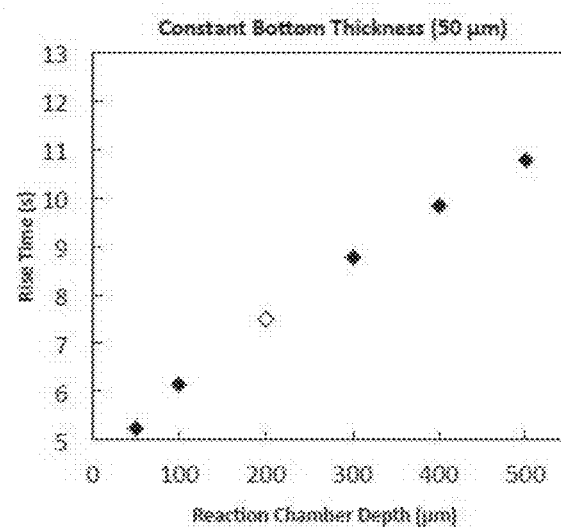
Figure 5C:
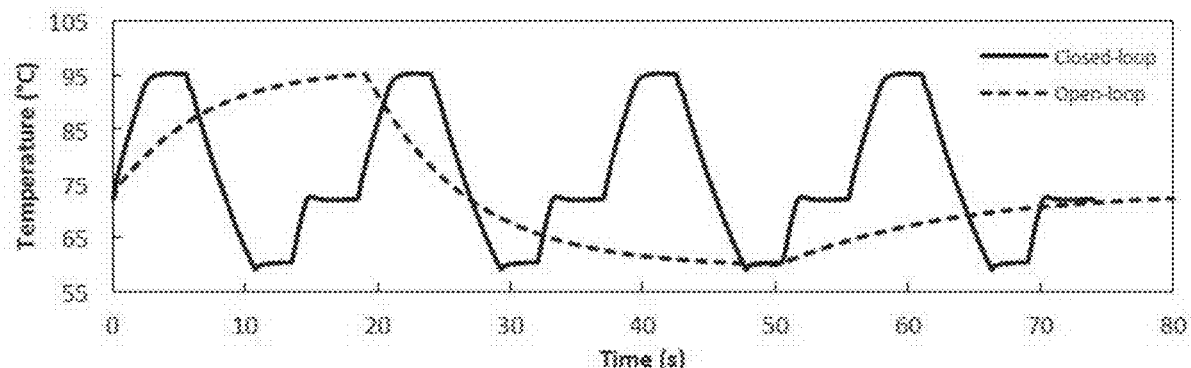
FIG. 5C demonstrates temperature vs. cycle time plots for the system using both open-loop and closed-loop control.

FIGS. 5A-5B result from a simulation model and allow to evaluate different chip designs by plotting the total rise time for a complete PCR cycle as a function of different chip parameters. Specifically, in FIG. 5A, the reaction chamber depth was kept constant at 200 µm while bottom thickness was varied from 50 to 400 µm. In FIG. 5B, the bottom thickness was kept constant at 50 µm while the reaction chamber depth was varied from 50 to 500 µm. FIG. 5C provides temperature vs. cycle time plots for the microfluidic chip of FIGS. 3A-3B using both open-loop (dashed line) and closed-loop (solid line) control system during a PCR reaction. The cycle time for closed-loop control system is 18.5 seconds, while the cycle time for open-loop control system is 80 seconds.

Based on results as presented in FIGS. 5A-5C, a direct correlation between each geometric parameter of the chip and the thermal rise time was observed, suggesting that smaller sealing layer thickness and chamber depth are desired. In one embodiment, chips were fabricated using a sealing layer thickness of 50 µm since the impact of this parameter on thermal response for lower thickness values is minimal. Sealing films below 50 µm proved challenging due to film deformation during bonding. In yet another embodiment, for the reaction chamber, a depth of 200 µm was selected as a tradeoff between rapid thermal response and high optical path length for sensitive fluorescence measurements. In practice, fluorescence intensity was not found to be a limiting factor for the system, indicating that further designs could further enhance thermal response times through the use of shallower reaction chambers.

Figure 11:
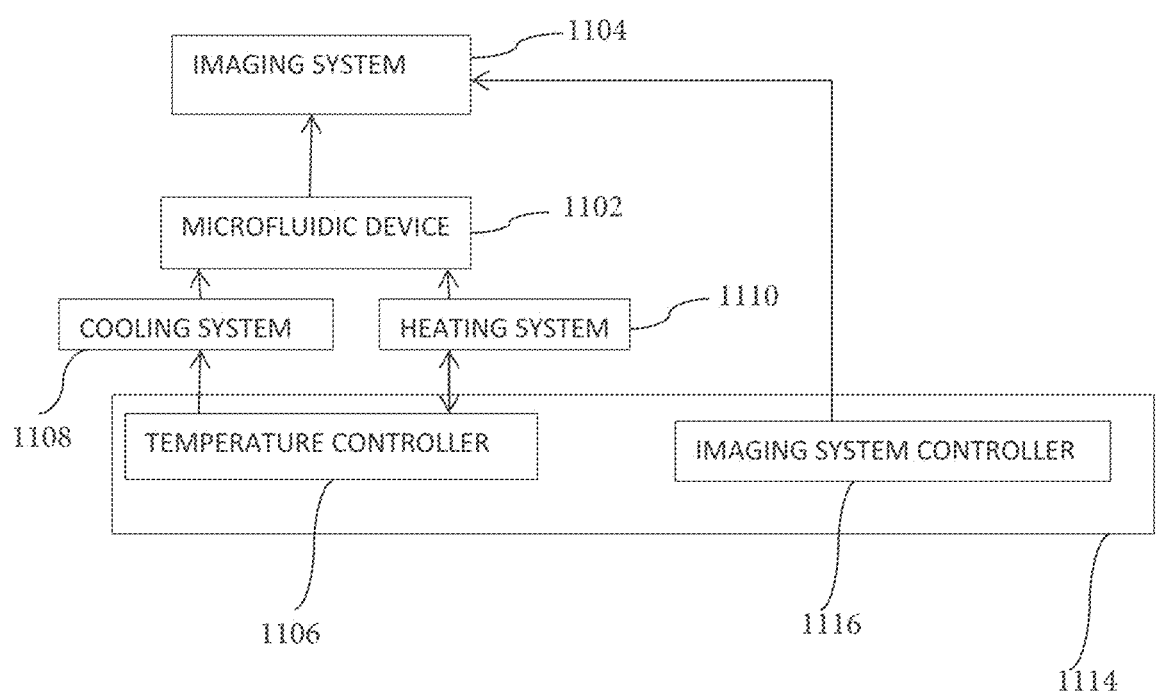
FIG. 11 is a block diagram of the microfluidic system according to the present invention.

The data in FIGS. 5A-5B is presented for open-loop control of a PCR reaction. FIG. 11 relates to closed-loop control of a PCR reaction and illustrates a functional block diagram of a system including a microfluidic device (chip) 1102 and a main controller 1114. A DNA sample is input in the microfluidic chip 1102 to undergo a PCR reaction and subsequent post-PCR analysis. The main controller 1114 includes a temperature controller 1106 and imaging system controller 1114. The temperature controller 1106 is configured to provide closed-loop control for all assay steps including thermocycling of the PCR chamber 108 (FIG. 1A). The temperature controller 1106, which may be a programmed computer or other microprocessor, sends signals to a heating system 1110, including the heater electrodes 104 (FIG. 1A), based on the temperature determined by the temperature sensors 122, 124 (FIG. 1A). In this way, the temperature in the PCR chamber 108 (FIG. 1A) can be maintained at a desired level. In one embodiment, the temperature controller 1106 provides instruction on controlling the temperature in the PCR chamber to minimize duration of a PCR cycle. By way of example and without limitation, the temperature controller 1106 may be a PID control system. Other aspects of suitable temperature control system in accordance with the present invention are disclosed in U.S. Pat. No. 9,061,278, incorporated herein by reference in its entirety.

According to some embodiments of the present invention, the PCR chamber 108 (FIG. 1A) may also be cooled by a cooling device 1108, which may also be controlled by the temperature controller 1106. In one embodiment, the cooling device 1108 may be a heat sink or forced convection air cooled device, for example. To monitor the PCR process and HRMA analysis that occur in the PCR chamber 108 (FIG. 1A), the microfluidic system according to the present invention may include an imaging system 1104 and an imaging system controller 1116. The imaging system 1104, including an image capturing device (by way of example and without limitation, CCD camera) and an excitation source (by way of example and without limitation, LED source), is in optical communication with the PCR chamber 108 (FIG. 1A) to acquire fluorescence images during a PCR reaction and HRNA analysis. Other aspects of a suitable imaging system in accordance with some aspects of the invention are disclosed in U.S. Pat. No. 8,058,054, incorporated herein by reference in its entirety.

The temperature controller 1106 dictates the input voltage applied to the heater electrodes based on feedback from temperature sensor electrodes built into the model. In one embodiment, when the control system is a PID control system, the PID parameters are optimized manually, with the maximum input voltage limited to account for the physical constraints of the actual heating elements and based on the fabricated chip dimensions. FIG. 5C produced by a simulation model demonstrates that closed-loop control significantly decreases the duration of a PCR cycle compared to open-loop control.

Figure 6:
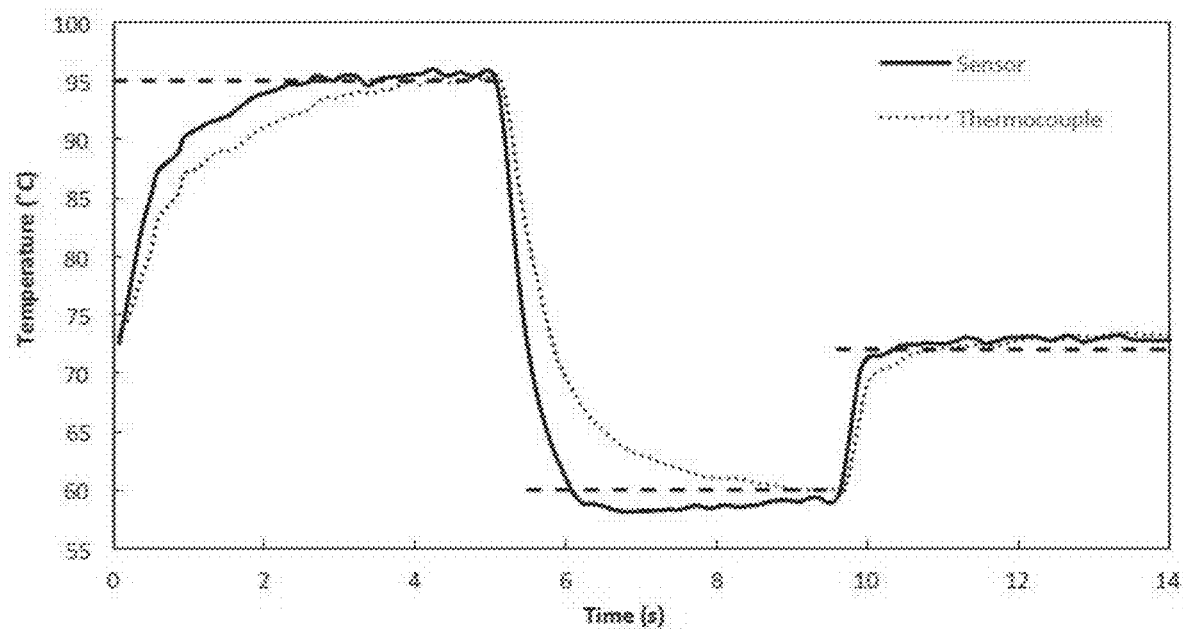
FIG. 6 demonstrates temperature vs. time plots acquired during a PCR cycle, the temperature measured by a thermocouple embedded into reaction chamber (dot line) and sensor electrodes (solid line), respectively.

To confirm the closed-loop numerical model used in FIG. 5C, thermal performance was characterized in a fabricated microfluidic chip according to the present invention (FIG. 1A and FIGS. 3A-3B) containing both thin film temperature sensors and a thermocouple embedded in the reaction chamber during chip sealing. PID parameters, identical to the parameters used in FIG. 5C, were used for the software-defined closed-loop control scheme executed by the temperature controller 1106. A comparison of model results with data from both the sensor electrodes and thermocouple is presented in FIG. 6. It is evident that the initial parts of both denature and anneal steps exhibit a dynamic offset between the thin film sensor and the reaction chamber thermocouple measurements. This offset is compensated for in software. Using this approach, a cycle time of 14 s was achieved, slightly faster than a modeled cycle time of 19 s when employing identical dwell times at each temperature set point, and well within our targeted time of 20 s per cycle.

In one embodiment, to produce the data as shown in FIGS. 5A-5C, a 3D model (by way of example and without limitation, Version 4.4, COMSOL, Burlington, Mass.) incorporating PID controls and chip design parameters was used to study thermal performance during each step (denature, anneal, and extension) of the PCR cycle. The PID algorithm used PCR step-specific parameters to maximize speed and control authority at each step. The input voltage, clipped to limit the current density through the thin film elements, was determined by using feedback from a temperature sensor electrode built into the model. Dimensions of the bottom COP film thickness and reaction chamber depth were varied over ranges that were selected based on material and fabrication process constraints. Forced air convection was incorporated into the model to represent high CFM fans blowing on the chip during operation, with convective heat flux parameters for the denature, anneal, and extension steps. In one embodiment, the convective heat flux parameters for denature, anneal, and extension steps were given by 40, 80, and 40 $W^2K^{-1}$, respectively. Rise time was determined using the model at each thermocycle step for each geometric design variation. The model was also used to compare cycle times under open-loop and closed-loop control. For closed-loop control, the input voltage was determined using a PID control algorithm and temperature feedback from the sensor element. Proportional, integral, and derivative controller constants were varied to optimize cycling speed and control authority at each PCR step. In one embodiment, total cycle times for both open-loop and closed-loop control included hold times at the denture, anneal, and extension steps of 2, 2, and 4 s, respectively.

In yet another embodiment, a microcontroller platform 1114 (FIG. 11) (by way of example and without limitation, Atmel ATmega328P-based platform, ProTrinket 5V, Adafruit, New York, N.Y.) was programmed to implement all assay control functions, including temperature sensing, control over voltage applied to the heating electrodes (for example PID control), and triggering of a detection system including CCD camera (by way of example and without limitation, DMK41BU02, Imaging Source, Charlotte, N.C.) and LED light source (by way of example and without limitation, 2600N-701-14-C2, Innovations in Optics, Woburn, Mass.) for fluorescence imaging. In one embodiment, the PID control algorithm outputs a pulse width modulated signal to adjust average DC power applied to the heaters with an n-type MOSFET. The integrated closed-loop temperature controller 1106 (FIG. 11) and data acquisition system 1104 (FIG. 11) were then used to implement software-defined PCR and HRMA routines.

In one embodiment, temperature sensing in the reaction (PCR) chamber 108 of the microfluidic chip according to FIG. 1A and FIGS. 3A-3B is performed by applying a small current to the sensor electrode 122 (FIG. 1A) while monitoring the voltage drop across the sensor 124 (FIG. 1A). The PCR chamber 108 is matched to a pair of heating electrodes 104, with a single sensor electrode placed between them (FIG. 1B). A low 1 mA current is used to prevent Joule heating of the sensor electrode. In one embodiment, gold is used for both the heating and sensing electrodes due to its linear temperature coefficient of resistance in the PCR temperature range. To maximize temperature resolution, a sensor interface was used to convert the raw input signal range to the full 5 V analog input range of the microcontroller using a level shift amplifier circuit to yield zero output voltage at 55° C. together with an instrumentation amplifier circuit with a voltage gain of 250. In a further embodiment of the present invention, the sensor interface circuit and microcontroller connections to the various system components were assembled on a custom circuit board with a total footprint below 8 cm square, including the microcontroller itself. Electrical connections between the controller board and thermoplastic chips are made with surface-mount gold-coated spring contact pins.

Before testing, each device is calibrated to enhance temperature accuracy. Chips were first burned in by looping the temperature between 23° C. and 95° C. for at least 3 cycles at a ramp rate of ±1° C./s, after which the temperature coefficient of resistance (TCR) for each chip is determined. The TCR is dependent on gold microstructure, which can vary within individual wafers, across multiple wafers in a single fabrication run, and between batches from different runs. Calibration was performed by placing the chips in an oven with a thermocouple and voltmeter attached to measure resistance and temperature. While in one embodiment this process was performed for individual chips, calibration can be readily automated for large numbers of chips in parallel.

Figure 10A:
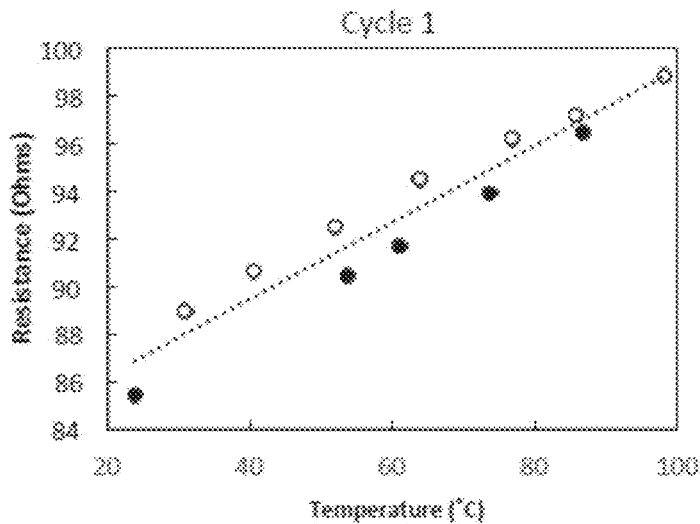
FIGS. 10A-10C demonstrates temperature versus resistance plots over three cycles, respectively (heating shown as white hollow dots, cooling shown as filled black dots).
Figure 10B:
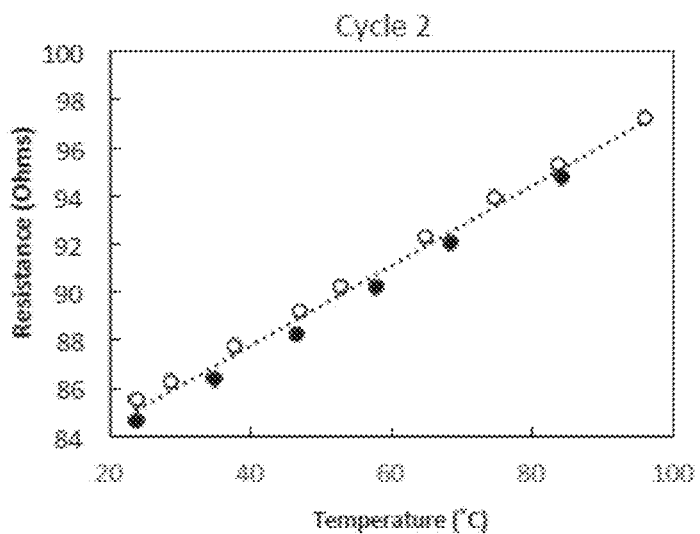
Figure 10C:
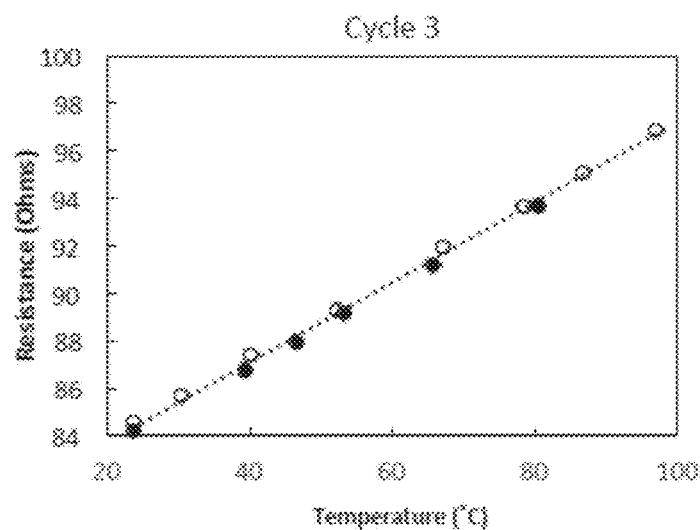

FIGS. 10A-10C represent heater resistance as a function of temperature during first, second, and third cycle, respectively. Burn-in of the electrodes is critical for achieving accurate temperature measurements and high sensing resolution. As demonstrated in FIG. 10A, prior to burn-in, significant hysteresis was observed for the sensors, with up to 3% variation in sensor resistance at 60° C. After three burn-in cycles (FIGS. 10A-10C), hysteretic variations were reduced to less than 2% within the full PCR temperature range. The TCR of each sensor was determined after burn-in for each individual chip. This calibration procedure is necessary due to large chip-to-chip variability. Even within a single COP wafer containing six individual microfluidic chips, nominal resistance values were found to vary with relative standard deviations up to 4%. Burn-in is a standard process step in the manufacture of many temperature sensors such as discrete thermistors, and can be implemented in a highly parallel process for low cost fabrication.

During PCR, fluorescence images are collected by the imaging system 1104 (FIG. 11) at the end of an extension step during each PCR cycle. Image data was communicated over a serial port to a computer and average fluorescence within the reaction chamber was plotted in real time. In one embodiment, the threshold cycle (Ct) was calculated independently for each data set as the cycle number at which the fluorescence signal reached a value of 20σ, where σ is the standard deviation of the fluorescence signal over cycles 3-15. After amplification, HRMA analysis was performed on the amplified nucleic acids. In one embodiment, during HRMA analysis, the chip temperature was ramped from 60° C. to 85° C. at a rate of 0.07° C./s with fluorescence images collected every 5 s. A spline curve was fit to the fluorescence data and the derivative of the curve is taken at each temperature point. The melting temperature (Tm) was determined as the temperature where the derivative is maximum.

A G6PC assay comprising forward and reverse primers together with custom master mix including DNA-intercalating dye is used to evaluate the microfluidic chip as demonstrated in FIGS. 3A-3B. The human G6PC gene is associated with type I glycogen storage disease (von Gierke's disease), a metabolic disorder resulting in the accumulation of glycogen and fat in body tissues and low blood glucose levels.

Example 2—PCR and HRMA in a Microfluidic Chip

A commercial G6PC assay (by way of example and without limitation, G6PC c.79delC Novallele Genotyping Assay, Canon U.S. Life Sciences, Inc., Rockville, Md.) was used to evaluate the microfluidic chip according to the present invention. By way of example and without limitation, samples of human genomic DNA (hgDNA) (id # NA11254) were purchased from Coriell Institute for Medical Research (Camden, N.J.). The G6PC primer set, mastermix, and hgDNA template were added in equal volumes to each reaction volume for a final concentration of 20 ng/μL. The hgDNA was diluted in Tris-EDTA buffer for the lower concentration reaction.

The software-defined PCR routine implemented by the microcontroller consisted of a 30 s hot start at 95° C., followed by 35 cycles of 95° C. for 5 s, 66° C. for 4.5 s, and 72° C. for 4.5 s. A final extension step at 72° C. for 30 s was performed on cycle 35. The total PCR run time was approximately 8.5 min. Separate chips were used to run the assay with $10^3$, $2\times10^3$, and $10^4$ copies of initial template. Identical dilutions at $10^4$ copies were run at both 30 s and 14 s cycle times to evaluate the impact of dwell times on amplification. The resulting amplification curves acquired at different initial target concentrations and cycle times are presented in FIG. 7A.

Figures 7A, 7B:
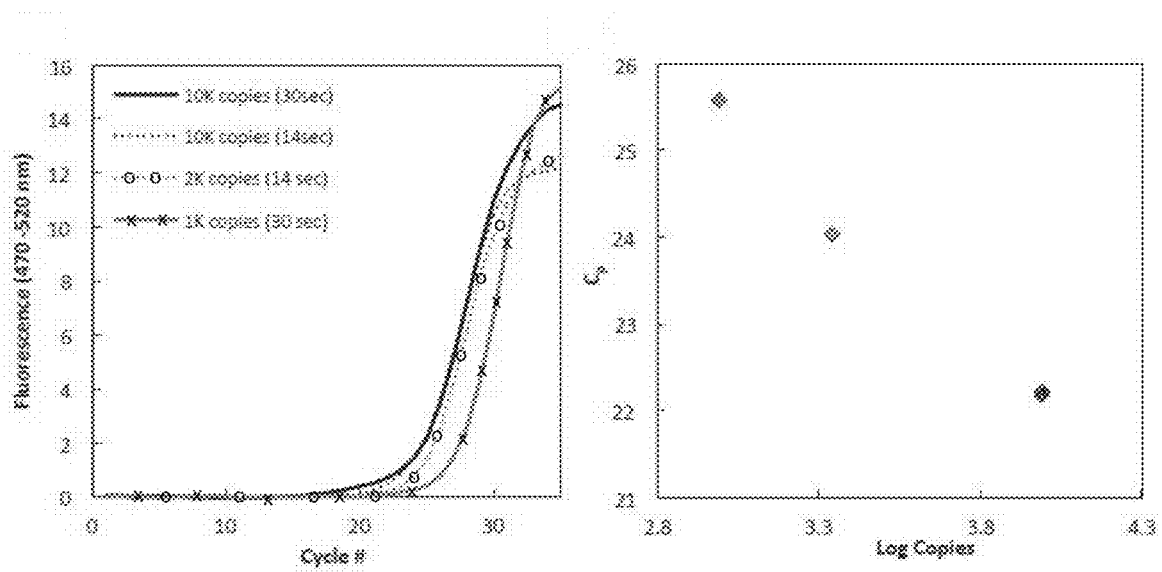
FIG. 7A demonstrates amplification curves for the PCR chip according to the present invention, the curves acquired for different concentrations and cycle times.
FIG. 7B is a plot of crossover point (Cp) vs. initial target concentration.

Extracted from the data of FIG. 7A Cp values (Cp, "crossover point" or "threshold cycle," refers to the number of cycles it took to detect a real signal from a sample) as a function of initial target concentration are shown in FIG. 7B. Cp values for each test are calculated by taking the standard deviation (σ) of the background fluorescence during cycle's 3-15 for each data set. This σ was multiplied by a factor of 20 to determine a threshold value for each independent data set. No difference in Cp was observed for the case of $10^4$ copies at 14 s and 30 s, indicating that the shorter cycle time is sufficient to achieve efficient on-chip amplification for the G6PC assay.

Figure 9:
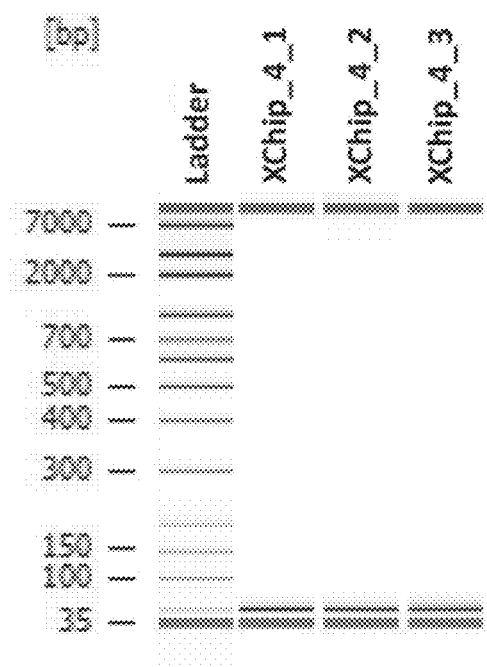
FIG. 9 demonstrates three experiments for G6PC amplification product run under high sensitivity electrophoresis.

In one embodiment, validation of PCR product was performed by using a capillary gel electrophoresis system (by way of example and without limitation, BioAnalyzer 2100, Agilent, Santa Clara, Calif.) in conjunction with an assay for detecting a single mutation in the human G6PC gene. To validate the reaction, capillary gel electrophoresis was performed on PCR product of the human G6PC gene extracted from three different microfluidic chips. The analysis, as shown in FIG. 9, revealed 51 bp fragments for the microfluidic chips, which compares well with a theoretical G6PC amplicon length of 45 bp.

Figure 8A:
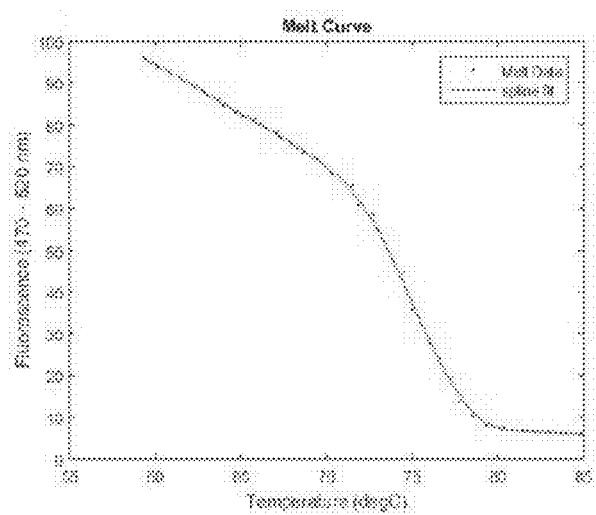
FIG. 8A is a plot of melt curve data collected on the chip according to the present invention after completing PCR amplification.
Figure 8B:
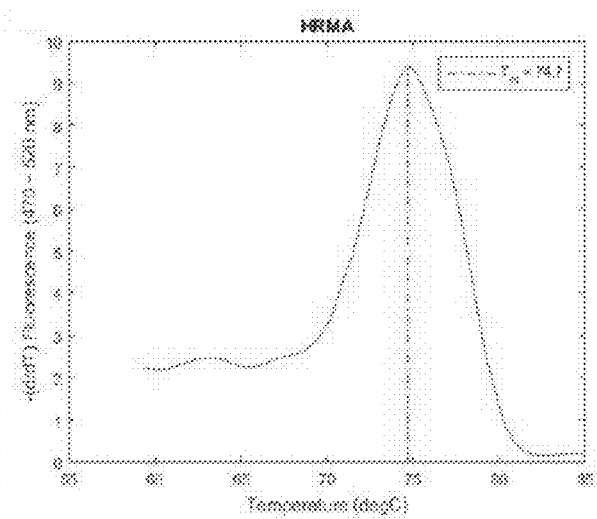
FIG. 8B demonstrates a derivative of the spline equation fitting the curve in FIG. 8A.

In yet another embodiment, validation of a PCR reaction performed on the microfluidic chip according to the present invention employed HRMA technique. Specifically, HRMA is performed in the PCR chamber 108 of the microfluidic device of FIGS. 3A-3B. In the HRMA technique, controlled denaturing of amplicons with high temperature resolution enables sequence-specific DNA melting temperatures to be evaluated. The melting temperatures provide additional information about the PCR product without the need for an additional instrumentation or use of a post-PCR assay. Using the integrated microfluidic chips according to the present invention, HRMA analysis was completed in 6 min. A typical melt curve resulting from on-chip HRMA analysis of the G6PC product immediately following PCR amplification is shown in FIG. 8A. Specifically, in FIG. 8A, the fluorescence measured during nucleic acid dissociation is presented as a function of the temperature. The curve in FIG. 8A was then fit with a spline to mitigate sensor noise that results in a non-smooth melt peak. HRMA analysis was done by taking the negative derivative of the spline fit equation at each respective data point and plotting the curve. The maximum (−dF/dT) in fluorescence is identified as the amplicon melting temperature. The final HRMA plot consisting of the derivative of the melt curve of FIG. 8A is presented in FIG. 8B. The average melting temperature determined for all tested devices was 75.14±0.45° C., which compares very well against the theoretical melt temperature.

Accordingly, a disposable microfluidic chip with integrated gold thin film heating and sensing electrodes is provided. By taking advantage of numerical modeling, an optimized chip design can achieve cycle times of 14 s, with a complete 35 cycle PCR assay including HRMA is performed in a total of 15 min. Amplification of hgDNA targeting a mutation in the G6PC gene indicative of von Gierke's disease was successfully performed using the thermoplastic chips, with on-chip HRMA serving to verify a mean G6PC melting temperature of 75.14° C.

The accompanying drawings, which are incorporated herein and form part of the specification, illustrate various non-limiting embodiments of the present invention.

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

As used herein, any descriptions of any type of genetic material can mean any nucleic acid, including DNA and RNA, in the alternative or the additive to the genetic material originally provided. Thus, genetic material may include a gene, a part of a gene, a group of genes, a fragment of many genes, a molecule of DNA or RNA, molecules of DNA or RNA, a fragment of a DNA or RNA molecule, or fragments of many DNA or RNA molecules. Genetic material can refer to anything from a small fragment of DNA or RNA to the entire genome of an organism.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A microfluidic system comprising:
a microfluidic chip comprising:
a first thermoplastic layer including at least one inlet well in fluid communication with a PCR chamber and one or more passive hydrophilic capillary valves, and wherein a passive hydrophilic expansion valve is located at an end of the PCR chamber opposite in position to the at least one inlet well;
a second thermoplastic layer having a first surface and a second surface, the first surface in direct contact with a heating element, the heating element controlling a temperature in the PCR chamber;
wherein the second surface of the second thermoplastic layer is bonded to the first thermoplastic layer sealing the PCR chamber;
a temperature controller controlling an input voltage applied to the one or more heater electrodes based on data provided by the one or more sensor electrodes indicative of the temperature in the PCR chamber; and
wherein the temperature controller executes software that adjusts the input voltage during each PCR cycle based on pre-selected temperature controller parameters to minimize a duration of each PCR cycle such that PCR is complete in less than 10 minutes.

2. The system of claim 1, wherein the temperature controller parameters are selected to minimize the duration of each PCR cycle.

3. The system of claim 2, wherein the temperature controller parameters are selected prior to performing a PCR reaction based on data produced by a simulation model evaluating thermal performance of the microfluidic chip during each stage of a PCR cycle.

4. The system of claim 1, wherein the heating element comprises one or more heater and sensor electrodes patterned on the first surface of the second thermoplastic layer.

5. The system of claim 1, further comprising a cooling device to cool the PCR chamber.

6. The system of claim 1, wherein the temperature controller is a PID controller.

7. The system of claim 1, wherein the first and second thermoplastic layers are fabricated from cyclic olefin polymer (COP) or cyclic olefin copolymer (COC).

8. The system of claim 1, wherein a sample received at the input well flows towards the PCR chamber by a capillary action, the sample fluid being halted at the PCR chamber by the one or more hydrophilic capillary valves.

9. The system of claim 1, wherein the second thermoplastic layer is 50 µm thick.

10. The system of claim 1, wherein the reaction chamber is 200 µm deep.

11. The system of claim 1, wherein the reaction chamber is matched to the one or more heater electrodes.

12. The system of claim 4, wherein temperature sensing in the reaction chamber is performed by applying a small current to a first sensor electrode while monitoring a voltage drop across a second sensor electrode.

13. The system of claim 1, wherein an expansion angle of the passive expansion valve is provided at 150°.

14. The system of claim 1, wherein the one or more valve(s) has a width of approximately 50 µm and a depth of approximately 20 µm.

15. The system of claim 1, wherein the thickness of the second thermoplastic layer and the depth of the reaction chamber are selected to minimize the duration of a PCR cycle.

16. The system of claim 1, wherein the PCR reaction in the reaction chamber is followed by a high resolution melt analysis (HRMA) performed in the PCR chamber.

* * * * *